US00PP20721P3

(12) United States Plant Patent
Skelton

(10) Patent No.: US PP20,721 P3
(45) Date of Patent: Feb. 2, 2010

(54) *ACTINIDIA CHINENSIS* PLANT NAMED 'Y368'

(50) Latin Name: *Actinidia chinensis*
Varietal Denomination: Y368

(76) Inventor: Donald Skelton, R D 1, Huntly (NZ)

( * ) Notice: Subject to any disclaimer, the term of this patent is extended or adjusted under 35 U.S.C. 154(b) by 0 days.

(21) Appl. No.: 12/072,483

(22) Filed: Feb. 26, 2008

(65) Prior Publication Data

US 2009/0217431 P1 Aug. 27, 2009

(51) Int. Cl.
*A01H 5/00* (2006.01)

(52) U.S. Cl. ..... Plt./156

(58) Field of Classification Search ..... Plt./156
See application file for complete search history.

*Primary Examiner*—June Hwu

(57) ABSTRACT

A new and distinct *Actinidia chinensis* cultivar named 'Y368' is disclosed, characterized by having distinctive yellow flesh fruit, moderate cropping and a seasonal harvest time of mid March. Additionally, the new variety produces fruit with very soft, slight pubescence and with distinctive square shoulders. The new variety is suitable for commercial production of kiwi fruit.

3 Drawing Sheets

Latin name of the genus and species: *Actinidia chinensis.*
Variety denomination: 'Y368.'

BACKGROUND OF THE INVENTION

The new cultivar is a product of a planned breeding program begun in 1975 under the direction of the inventor, Donald Alfred Skelton, a citizen of New Zealand. The seed parent is the unpatented, proprietary seedling variety referred to as *Actinidia chinensis* 'A124' The pollen parent is the unpatented, proprietary seedling variety referred to as *Actinidia chinensis* 'RY.'

Fruit of the new variety was first evaluated in 1999 with favorable results. After the first evaluation, semi-hardwood cuttings were made of 'Y368' and were grafted onto 5 seedling rootstocks 3; of *A. chinensis* and 2 of *A. deliciosa*. Evaluation, asexual propagation and grafting all first took place at the inventor's commercial nursery in Rangiriri, New Zealand in 1999. Subsequent evaluations of the variety have shown the characteristics to be true to type.

SUMMARY OF THE INVENTION

The cultivar 'Y368' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Y368' These characteristics in combination distinguish 'Y368' as a new and distinct *Actinidia chinensis* cultivar:

1. Distinctive yellow flesh fruit
2. Seasonal harvest time of mid March
3. Very soft, downy pubescence on fruit, with weak adherence to the fruit skin.
4. Oblong fruit shape.
5. Fruit with a distinctive blunt stylar end shape and square shoulders.
6. Circular median shape in cross section.

COMPARISON TO PARENT

Plants of the new cultivar 'Y368' are similar to plants of the seed parent, *Actinidia chinensis* 'A124' in most horticultural characteristics, however, plants of the new cultivar 'Y368' produce significantly different shaped fruit, including differences in the overall fruit shape and with different stylar end characteristics.

Plants of the new cultivar 'Y368' are similar to plants of the male parent, *Actinidia chinensis* 'RY' in most horticultural characteristics, however, plants of the new cultivar 'Y368' produce significantly more female flowers than the male parent. Whereas the new cultivar produces large quantities of female flowers, the male parent produces almost no viable female flowers.

COMMERCIAL COMPARISON

The new variety is best compared to the commercial variety, 'Hort16A,' USPP 11,066. 'Y368' is similar to 'Hort16A' in many horticultural characteristics, however, 'Y368' produces mature approximately 6 weeks earlier than 'Hort16A.' Additionally, the new variety produces an oblong shaped fruit, compared to ovoid. Fruit of the new variety 'Y368' are distinctively blunt on the stylar end, compared to the strong pointed stylar end shape of 'Hort16A.' Fruit shape differences can also be noted in the shoulder shape. Whereas 'Y368' produces fruit with strongly squared shoulder, 'Hort16A' fruit have rounded shoulders. The median cross-section of 'Y368' is a very distinctive circular shape, whereas 'Hort16A' is elliptic.

BRIEF DESCRIPTION OF THE PHOTOGRAPH

The accompanying photograph in FIG. 1 illustrates in full color typical foliage and flowers on plants of 'Y368.'

Figure 1:
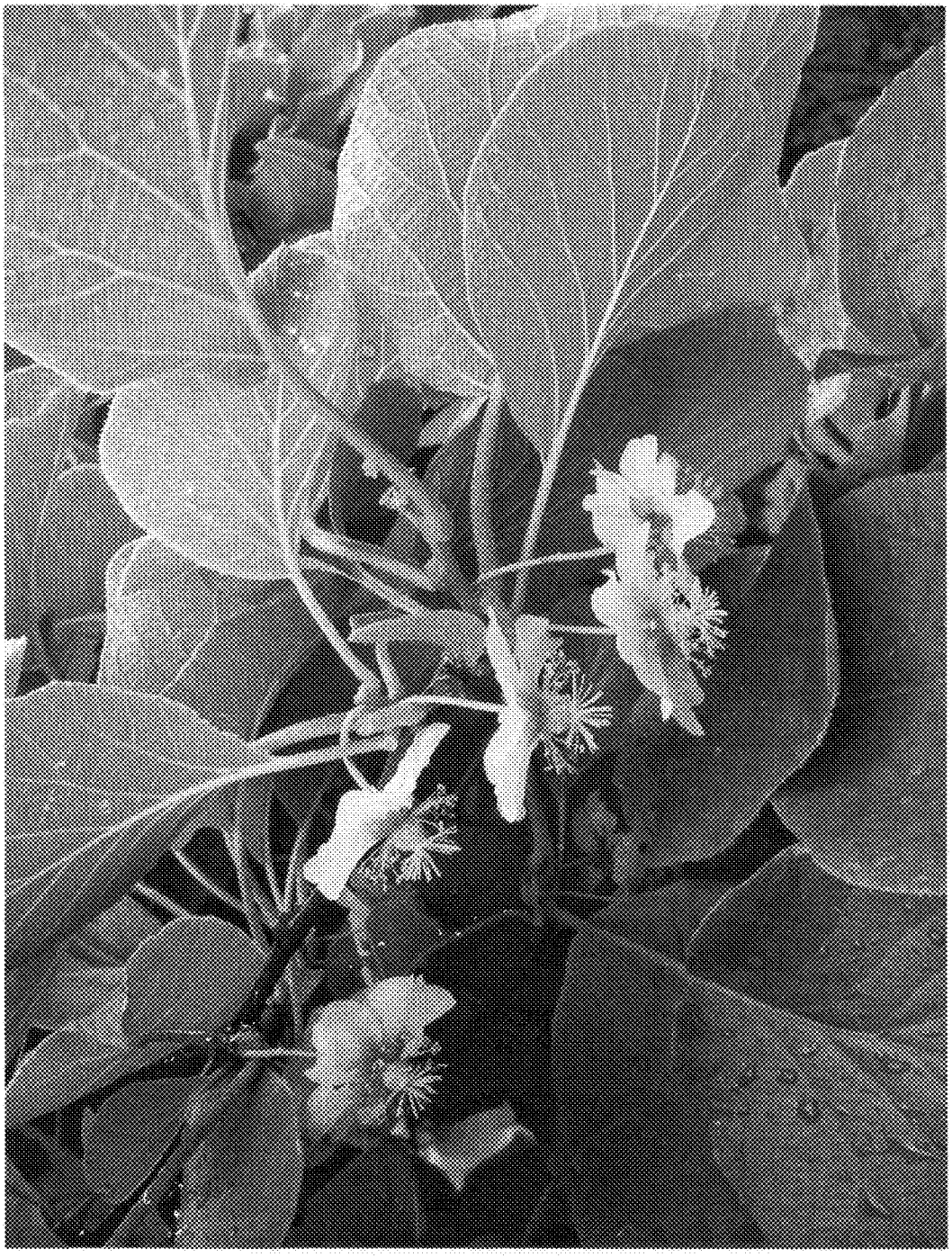
Figure 2:
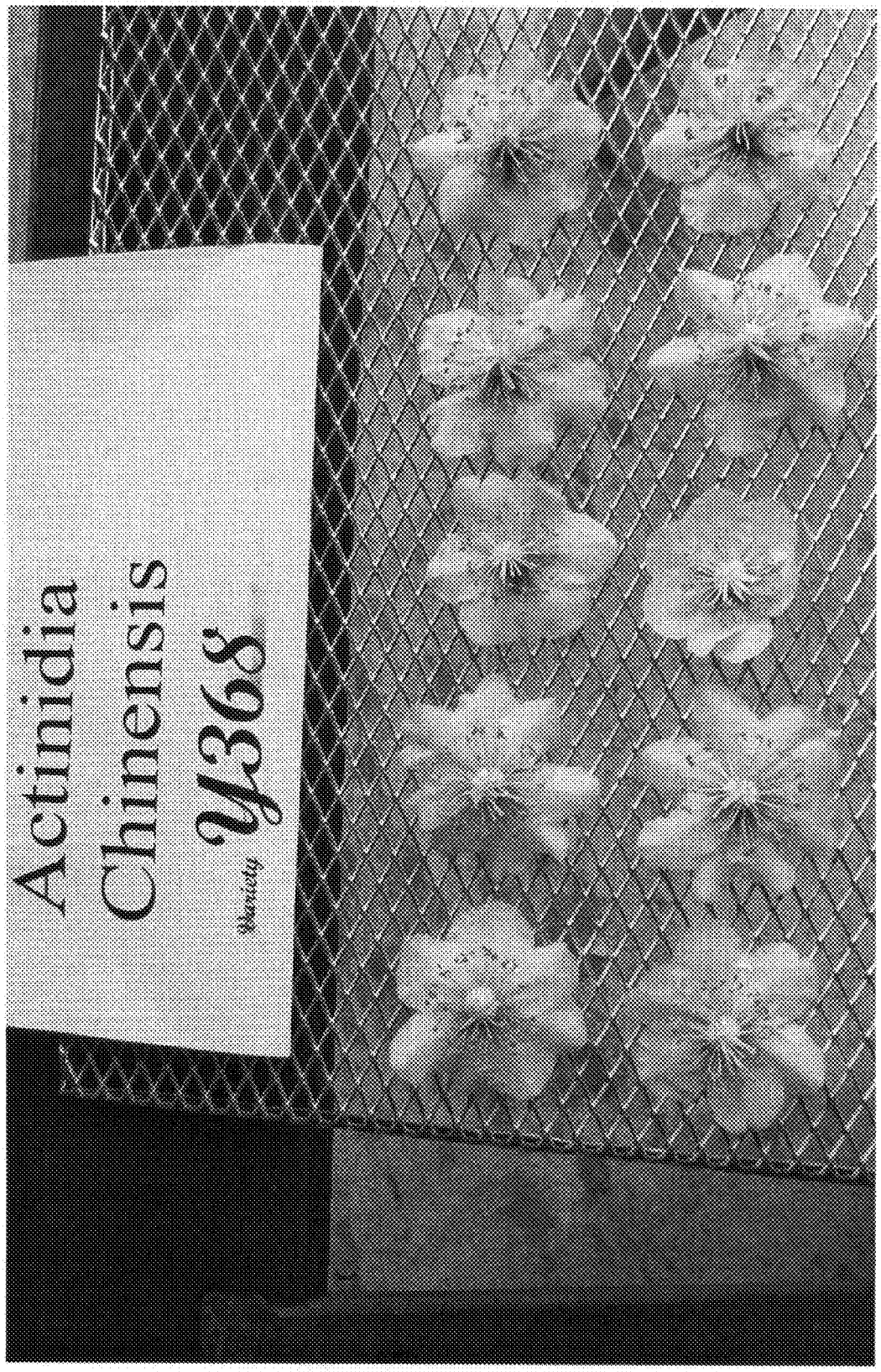
FIG. 2 illustrates in full color typical flowers of 'Y368.'
Figure 3:
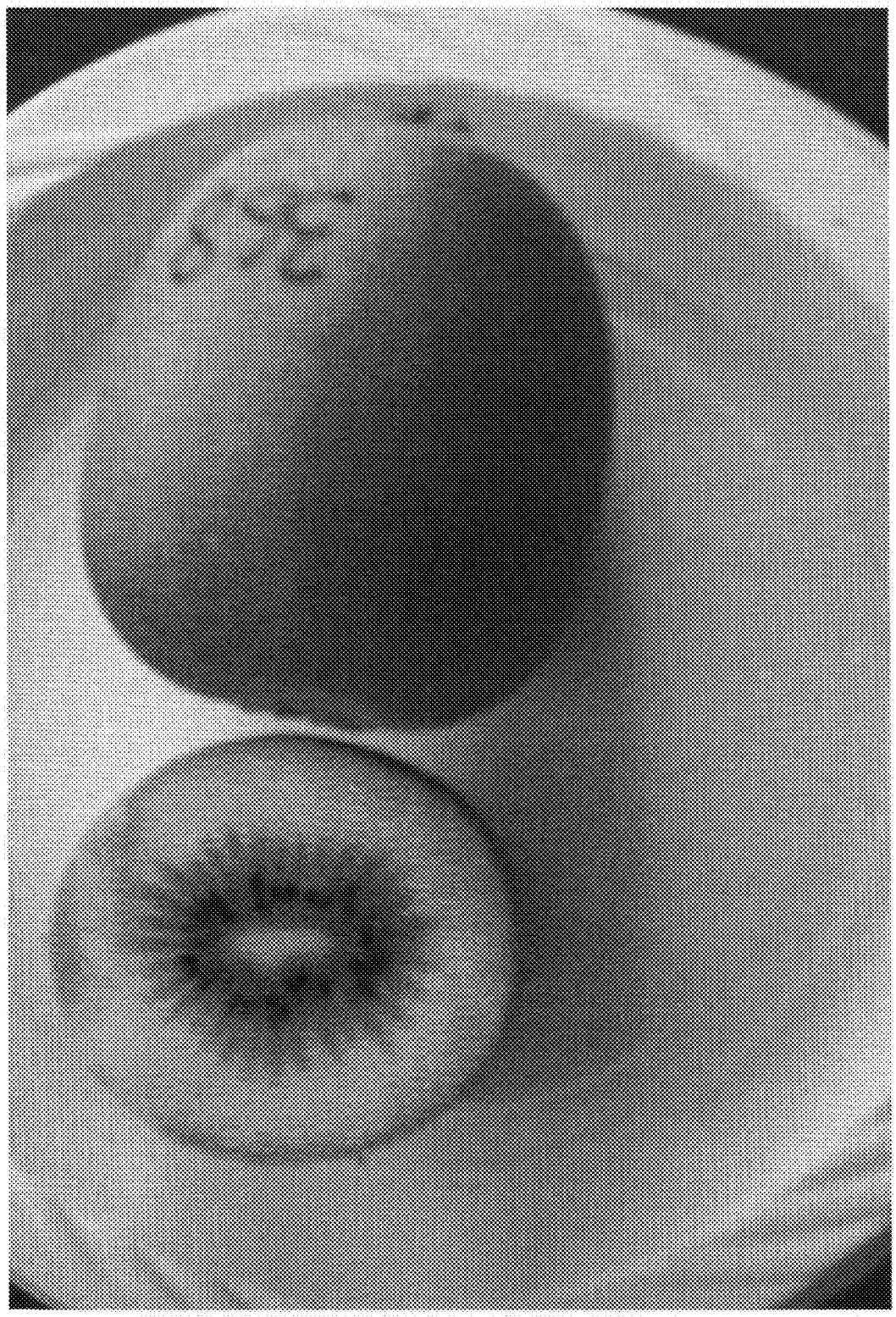
FIG. 3 shows examples of typical fruit harvested from 'Y368.'

All photographs are taken of plants approximately 7 years old. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Y368' plants grown under commercial trial conditions in Rangiriri New Zealand. The growing temperature ranged from 10° C. to 25° C. with no precipitation. Measurements and numerical values represent averages of typical plant types.

Botanical classification: *Actinidia chinensis* 'Y368.'

PROPAGATION

'Y368' can be successfully grafted onto rootstocks of *Actinidia chinensis* or *Actinidia deliciosa.*

PLANT

*Age of the plant described.*—Approximately 7 years.
*Sex expression.*—Female.
*Ploidy.*—Diploid.
*Vigor.*—Moderately high vigor. On a scale of 1 to 10 with 10 being the highest 'Y368' is a comparative 8 among commercial *Actinidia* varieties.
*Young shoot color.*—Near RHS Green 137C.
*Young shoot texture.*—Smooth, non-pubescent and no visible lenticels.
*Stem diameter.*—Average 1 cm.
*Stem texture.*—Rough.
*Trunk diameter.*—Average 5 cm on a 7 year old plant.
*Stem lenticels.*—Stem lenticels either not present or barely visible to the eye.

FOLIAGE

Leaf:
*Average length.*—Range between 17.4–17.5 cm.
*Average width.*—Range between 14.8–15.5 cm.
*Shape of blade.*—Very broadly ovate.
*Apex.*—Rounded.
*Base.*—Cordate, overlapping.
*Attachment.*—Petioled.
*Margin.*—Ciliate.
*Texture of top surface.*—Slightly puckered. Non-pubescent.
*Texture of under side.*—Moderately glossy, non-pubescent.
*Color.*—Mature foliage upper side: Near RHS Green 137C. Mature foliage under side: Near RHS Green 141C.
*Petiole.*—Length: Range between 14.8–15.5 cm. Pubescence: None. Color: Near RHS Yellow-Green 145B with a strong flush of Red-Purple 60D on upperside of petiole.

FLOWER

*Flowers per inflorescence.*—Most often 3.
*Bud color.*—Near RHS Yellow-Green 145A.
*Bud break.*—Early September.
*First flower.*—Early October.
*Diameter.*—Average 4.7 cm.
*Petal quantity.*—6 to 8 per flower.
*Petals overlapping.*—Yes.
*Color.*—Near RHS White 155A.
*Filament color.*—White.
*Anther color.*—Light brown.
*Attitude of styles.*—Semi-erect.
*Style color.*—Near RHS White 155C.
*Style quantity.*—Average 24.
*Hair on ovary.*—Dense.
*Color of ovary.*—White.
*Number of sepals.*—6 to 8.
*Color of sepals.*—Near RHS Yellow-Green 144D.
*Sepal width.*—Approximately 1.1 cm.
*Sepal length.*—Approximately 0.6 cm.
*Sepal texture.*—Smooth.

Peduncle:
*Length.*—Average 5.5 cm.
*Color.*—Near RHS Yellow-Green 145A.
*Texture.*—Smooth.

FRUIT

*Color outer pericarp.*—Near RHS Yellow 3B.
*Color inner pericarp.*—Near RHS Yellow 3A.
*Core color.*—Near RHS White 155A.
*Brix at consumption.*—16.0–17.0.
*Brix at harvest.*—7.20%.
*Average weight.*—110 grams.
*Minimum weight.*—98 grams.
*Maximum weight.*—125 grams.
*Length.*—Avg. 67 mm.
*Width.*—Avg. 59 mm.
*Core diameter(maximum).*—14.0 mm.
*Core diameter(minimum).*—8.0 mm.
*Locule number.*—30.
*Fruit peduncle length.*—43 mm.
*Fruit peduncle width.*—3.5 mm.
*General shape.*—Oblong.
*Median cross section.*—Circular.
*Stylar end shape.*—Slightly blunt protruding.
*Shoulder shape.*—Squared.
*Calyx ring.*—Present.
*Calyx ring expression.*—Strong.
*Skin color at harvest.*—Near RHS Grey-Brown 199C.
*Hair on fruit skin.*—Downy.
*Hair adherence to skin.*—Weak.
*Skin adherence to flesh at maturity.*—Moderate.
*Fruit core shape.*—Transversely elliptic.
*Core-woody spike.*—Medium.
*Lenticels on fruit.*—Not present.
*Mature seed color.*—Black.
*Dried seed.*—Brown.
*Harvest time.*—Mid March.
*Overall cropping quantity.*—Moderate.

OTHER CHARACTERISTICS

Storage life.—Storage life is a minimum of 3 months at 2° C.
Disease/pest resistance.—Neither resistance nor susceptibility to pathogens and pests common to *Actinidia chinensis* have been observed.
Temperature tolerance.—Tolerates low temperatures to approximately −8° C. without negative effects, tolerates high temperatures to approximately 35° C. without negative effects.

What is claimed is:

1. A new and distinct cultivar of *Actinidia chinensis* plant named 'Y368' as herein illustrated and described.

* * * * *